United States Patent [19]

Neurath

[11] Patent Number: 4,591,552
[45] Date of Patent: May 27, 1986

[54] DETECTION OF HEPATITIS B SURFACE ANTIGEN (OR ANTIBODY TO SAME) WITH LABELED SYNTHETIC PEPTIDE

[75] Inventor: A. Robert Neurath, New York, N.Y.

[73] Assignee: New York Blood Center, Inc., New York, N.Y.

[21] Appl. No.: 426,309

[22] Filed: Sep. 29, 1982

[51] Int. Cl.$^4$ ............................................. G01N 53/00
[52] U.S. Cl. .................................. 435/7; 436/534; 436/804; 436/820; 436/828; 530/321; 530/324; 530/326; 530/806
[58] Field of Search .................... 435/7; 436/828, 534, 436/804, 820; 260/112.5 R

[56] References Cited

U.S. PATENT DOCUMENTS

| | | | |
|---|---|---|---|
| 3,995,018 | 11/1976 | Sjoquist | 436/828 X |
| 4,016,043 | 4/1977 | Schuurs | 435/7 |
| 4,272,433 | 6/1981 | Nishino | 260/112.5 R |
| 4,277,393 | 7/1981 | Sakakibara | 260/112.5 R |
| 4,297,273 | 10/1981 | Buckler et al. | 260/112 B |
| 4,341,761 | 7/1982 | Ganfield | 260/112.5 R |
| 4,369,138 | 1/1983 | Lindall | 260/112.5 R |
| 4,377,516 | 3/1983 | Goldberg | 260/112.5 R |
| 4,399,229 | 8/1983 | Kelton | 436/828 X |
| 4,409,141 | 10/1983 | Noda | 260/112.5 R |
| 4,415,491 | 11/1983 | Vyas | 260/112.5 R |
| 4,415,546 | 11/1983 | Ramachandran | 260/112.5 R |
| 4,423,034 | 12/1983 | Nakagawa | 260/112.5 R |

OTHER PUBLICATIONS

Bhatnagar, P. K. et al., Proc. Natl. Acad. Sci. USA, 79(14), 4400–4404 (Jul. 1982).
Peterson, D. L. et al., J. Biol. Chem., 257(17), 10414–10420 (Sep. 10, 1982).
Neurath, A. R. et al., Proc. Natl. Acad. Sci. USA, 79(24), 7871–7875 (Dec. 1982).
T. P. Hop, "A Synthetic Peptide with Hepatitis B Surface Antigen Reactivity", Mol. Imm., vol. 18, No. 9, pp. 869–872 (1981).
C. R. Dreesman et al., "Antibody to Hepatitis B Surface Antigen . . . ", Nature, vol. 295, pp. 158–160 (Jan. 14, 1982).
A. R. Neurath and N. Strick "Localization of a Hepatitis B Surface Antigen Determinant Deduced from Results of Chemical Modifications", J. Virol, Methods, 3, 115–125, 1981 Elsevier/North–Holland Biomedical Press.
T. P. Hopp and K. R. Woods, "Prediction of Protein Antigenic Determinants from Amino Acid Sequences", Proc. Natl. Acad. Sci. 78, pp. 3824–3828, Jun. 1981-Immunology.
C. L. Lee and M. Z. Atassi, "Delination of the Third Antigenic Site of Lysozyme by Application of a Novel, 'Surface-Simulation' Synthetic Approach Directly Linking the Conformationally Adjacent Residues Forming the Site" Biochem. J. 159, pp. 89–93, 1976.
M. M. Hardy and D. M. Moore, "Neutralization of Foot-and-Mouth Disease Virus. I. Sensitization of the 140 S Virion by Antibody Also Reactive with the 12 S Protein Subunit", J. Gen. Virol., 55, pp. 415–427 1981.
R. J. Massey and G. Schochetman, "Viral Epitopes and Monoclonal Antibodies: Isoltion of Blocking Antibodies that Inhibit Virus Neutralization", Science, 213, pp. 447–450, 1981.
F. Audibert et al., "Active Antitoxic Immunization by a Diphtheria Toxin Synthetic Oligopeptide" Nature, 289, pp. 593–594, 1981.
J. Arnon, "Chemically Defined Antiviral Vaccines", Ann. Rev. Microbiol., 34, pp. 593–618, 1980.

(List continued on next page.)

*Primary Examiner*—Sidney Marantz
*Attorney, Agent, or Firm*—Sprung Horn Kramer & Woods

[57] ABSTRACT

A radiolabeled or enzyme labeled peptide having no more than 60 amino acids in the chain of the peptide; the peptide having covalently linked amino acids disposed in a steric configuration which is recognized by and bound by an antibody. The labeled peptides can be utilized in various processes to detect the presence of a given antibody or antigen in a sample. Hepatitis B surface antigen and antibody to same may be so detected.

8 Claims, 2 Drawing Figures

OTHER PUBLICATIONS

A. L. Kazim and M. Z. Atassi "A Novel and Comprehensive Synthetic Approach for the Elucidation of Protein Antigenic Structures", Biochem. J. 191, pp. 261-264, 1980.

R. A. Lerner, Nicola Green, Hannah Alexander, Fu-Tong Liu, J. Gregor Sutcliffe & Thomas M. Shinnick "Chemically Synthesized Peptides Predicted from the Nucleo-Tide Sequence of the Hepatitis B Virus Genome Elicit Antibodies Reactive with the Native Envelope Protein of Dane Particles", Proc. Natl. Acad. Sci. USA, vol. 78, No. 6, pp. 3403-3407, Jun. 1981, Biochemistry.

A. R. Neurath and N. Strick, "Enzyme-Linked Fluorescence Immunoassays Using Beta-Galactosidase and Antibodies Covalently Bound to Polystyrene Plates", J. Virol Methods, 1981, 3, pp. 155-165.

R. Arnon, M. Sela, M. Parant and L. Chedid, "Antiviral Response Elicited by a Completely Synthetic Antigen with Built-in Adjuvanticity", Proc. Natl. Acad. Sci USA, vol. 77, No. 11, pp. 6769-6772, 1980.

H. Arnheiter, R. M. Thomas, T. Leist, M. Fountlakis and B. Gutte, "Physicochemical and Antigenic Properties of Synthetic Fragments of Human Leukocyte Interferon", Nature, vol. 294, No. 19, 1981, pp. 278-280.

F. Schimizu, Y. Ohmoto and K. Imagawa, "Production of Anti-IFN-Beta Sera with Chemically Synthetic IFN-Beta Peptide Fragment (1-13), Biochem and Biphys. Res. Comm., vol. 103, pp. 1149-1156, 1981, No. 4.

J. G. Sutcliffe, T. M. Shinnick, N. Green, F.-T. Liu, H. L. Ninan and R. A. Lerner, "Chemical Synthesis of a Polypeptide Predicted from Nucleotide Sequence Allows Detection of a New Retroviral Gene Product", Nature, 287, 1980, pp. 801-805.

T. W. Wong and Allan R. Goldberg "Synthetic Peptide Fragment of src Gene Product Inhibits the src Protein Kinase and Crossreacts Immunologically with Avian onc Kinases and Cellular Phosphoproteins" Proc. Natl. Acad. Sci. USA, vol. 78, No. 12, pp. 7412-7416, 1981 Biochem.

J. L. Bittle, R. A. Houghten, H. Alexander, T. M. Shinnick, J. G. Sutcliffe, R. A. Lerner, D. J. Rowlands and F. Brown, "Protection Against Foot-and-Mouth Diseases by Immunization with a Chemically Synthesized Peptide Predicted from the Viral Nucleotide Sequence", Nature, vol. 298, pp. 30-33, 1982.

D. C. Jackson, J. M. Murray, D. O. White, C. N. Fagan and G. W. Tregear, "Antigenic Activity of Synthetic Peptide Comprising the 'Loop' Region of Influenza Virus Hemagglutinin", Virology, 120, pp. 273-276, 1982.

G. M. Müller, M. Shapira and R. Arnon, "Anti-Influenza Response Achieved by Immunization with a Synthetic Conjugate", Proc. Natl Acad. Sci. USA 79, pp. 569-573 1982, Immunology.

G. Walter, M. A. Hutchinson, T. Hunter and W. Eckhart "Purification of Polyoma Virus Medium-Size Tumor Antigen by Immunoaffinity Chromatography", Proc. Natl. Acad. Sci. USA, 79, pp. 4025-4029., Jul. 1982 Biochemistry.

M. H. Baron and D. Baltimore, "Antibodies Against a Synthetic Peptide of the Poliovirus Replicase Protein; Reaction with Native, Virus-Encoded Proteins and Inhibitions of Virus-Specific Polymerase Activities in Vitro", Jour. Virology, vol. 43, No. 3, pp. 969-978, 1982.

G. Walter, K-H. Scheidtmann, A. Carbone, A. P. Laudano and R. F. Doolittle, "Antibodies Specific for the Carboxy- and Amino-Terminal Regions of Simian Virus 40 Large Tumor Antigen", Proc. Natl. Acad. Sci USA, vol. 77, No. 9, pp. 5179-5200, 1980, Biochemistry.

A. Aitken and C. Hannoun, "Purification of Haemagglutinin and Neuraminidase from Influenza Virus Strain 3QB and Isolation of a Peptide from an Antigenic Region of Haemagluttinin", Eur. J. Biochem., 107, pp. 51-56, 1980.

F. Audibert, M. Jolivet, L. Chedid, R. Arnon and M. Sela, "Successful Immunization with a Totally Synthetic Diphtheria Vaccine", Proc. Natl. Acad. Sci. USA, vol. 79, pp. 5042-5046, 1982, Immunology.

E. H. Beachey, J. M. Seyer, D. B. Dale, W. A. Simpson and A. H. Kang, "Type Specific Protective Immunity Evoked by Synthetic Peptide of Streptococcus Pyrogenes M Protein", Nature, vol. 292, pp. 457-459, Jul. 1981.

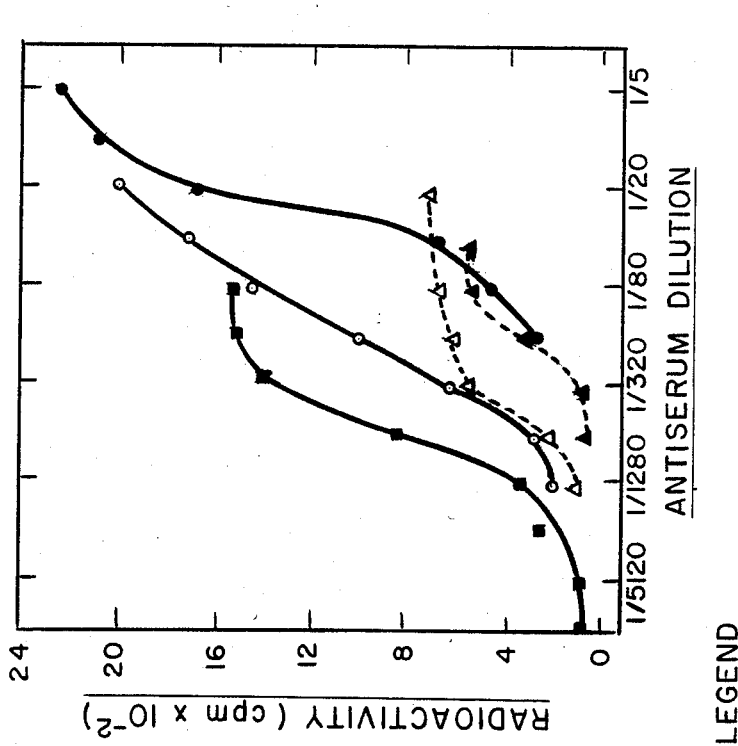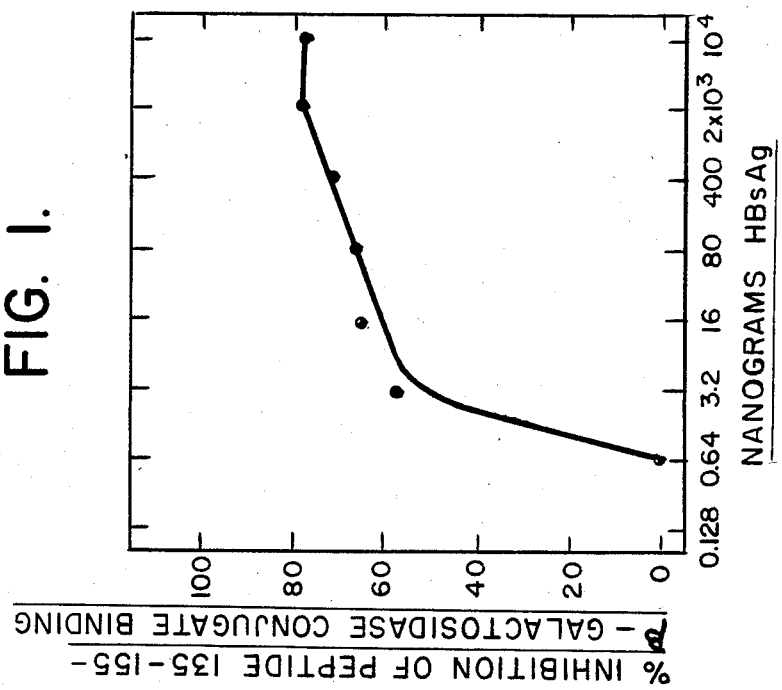

DETECTION OF HEPATITIS B SURFACE ANTIGEN (OR ANTIBODY TO SAME) WITH LABELED SYNTHETIC PEPTIDE

FIELD OF THE INVENTION

This invention relates to radiolabeled or enzyme labeled peptides and the use of such peptides as diagnostic reagents. More particularly, the present invention concerns processes for detecting antibodies or antigens in a sample by utilizing these novel peptides.

BACKGROUND OF THE INVENTION

An antigen is a substance causing a specific response in which resistance to a particular foreign substance develops after initial exposure to it. Antigens may be proteins, polysaccharides, nucleic acids, lipids, synthetic polymers and microorganisms, just to name a few. Antigens are characterized by a certain minimum size. Antigens may be as small as 1,000 daltons or as large as millions of daltons.

Upon exposure to an antigen, specific responses develop in a human or animal, one of which is the synthesis and releasing of antibodies from the lymphocytes and plasma cells. Antibodies are specific protein reagents that combine with antigens.

There are five classes of human antibodies (immunoglobulins), namely, IgA, IgD, IgE, IgG and IgM.

An antibody can bind to only a relatively small exposed portion of the surface of the antigen. This small reactive portion is said to be the antigenic determinant (epitope). An antibody is thus constructed to fit a particular exposed arrangement of chemical groups in the antigen, and it will not fit other regions of the antigen's surface. The binding site of an antibody will often "recognize" determinants of closely related structures with at least a partial fit into the site, but in general the tightest combination of antibody and antigen is achieved only when the fit is very good and complete. Accordingly, any synthetic reagent for the detection of antigens or antibodies must have a similar configuration to the corresponding natural antigenic determinant so as to be recognized by and to bind with the antibodies.

The upper limit on the size of antigenic determinants as estimated from studies on linear polypeptides, is about 30×17×6.5 Angstroms, or a volume of about 3,000 cubic Angstroms. The size of the antigenic sites on proteins is generally of the same magnitude, but these sites may also involve amino acids which are not sequentially arranged, but which are in close proximity due to the folding of the polypeptide chain.

An antigen such as a monomeric protein may contain more than a single antigenic determinant. Because of its limited size, the surface (volume) of the antigenic determinant represents only a minor fragment of the surface of the whole protein.

The amino acid residues corresponding to antigenic determinants contributing the highest proportion of the binding energy between an antigen and an antibody are referred to as the immunodominant group. In viral capsids and complex proteins (polymers), identical or nonidentical monomeric units interact in a way that involves part of their total surface. Any antigenic determinants occurring in this part of the monomers (viral structural components) are hidden and become available only upon disaggregation of the polymers. Such antigenic determinants are referred to as cryptotopes.

Antigenic determinants which are available at the surface of both of the polymers and the monomers are referred to as metatopes. The proper assembly of identical or non-identical monomers into polymers may result in the appearance of different antigenic determinants. These antigenic determinants may be comprised of amino acid residues from different monomers, or they may arise from conformational changes in the monomers such as, for example, allosteric transitions. Such antigenic determinants are referred to as neotopes.

The immunoinactivation of virus infectivity, for example, results from the combination of antibodies with surface antigen(s) on the virus particle. Consequently, metatopes and/or neotopes play the essential role in eliciting anti-viral antibodies in immunized humans or animals. If neotopes were absolutely essential, or if they played an immunodominant role, antibodies formed as a result of the immunization with monomers either would completely fail to neutralize the virus or would, perhaps, have low avidity (as measured by neutralization of virus infectivity). Considering the above, it is noted that neotopes may arise not only from the complete assembly of monomers (viral structural components) into a final polymer (viral capsid or envelope), but also from a limited association of a few identical or nonidentical monomers.

Hydrophilic (polar) amino acid side chains usually occur more frequently on the surface of proteins exposed to the surrounding medium, than in a position where they are shielded from the medium. Therefore, such amino acid residues are likely to represent antibody binding sites.

It has been suggested that in the evolution of viruses the most type-specific antigens became located on the outermost parts of the viral structure. Following this concept, neotopes and metatopes should have developed into highly type-specific antigenic determinants, while cryptotopes should be common for a certain group of viruses. In other words, neotopes and metatopes should be part of a variable amino sequence, and cryptotopes, part of a relatively invariable amino sequence within the evolving amino sequences of the constituent polypeptide chains of viral proteins.

The availability of amino acid sequence data (most easily deduced from the determination of the nucleotide sequence of the gene coding for the particular protein antigen) for protein antigens of pathogenic organisms has lead to attempts to identify the amino acid sequence corresponding to the immunodominant determinant, synthesize the corresponding sequence and utilize it as a synthetic vaccine, R. Arnon, "Chemically Defined Antiviral Vaccines", *Ann. Rev. Microbiol.*, 34, 593–618, 1980.

Amino acid sequences can be identified on the basis of the following: (1) by immunological studies on fragments of protein antigens obtained by cleavage with proteolytic enzymes or chemical reagents; (2) by synthesis of a series of consecutive overlapping peptides that represent the entire primary structure of the protein, A. L. Kazim and M. Z. Atassi, "A Novel and Comprehensive Synthetic Approach for the Elucidation of Protein Antigenic Structures", *Biochem. J.*, 191, 261–264, 1980; R. A. Lerner, "Chemically Synthesized Peptides Predicted From the Nucleotide Sequence of the Hepatitis B Virus Genome Elicit Antibodies Reactive With the Native Envelope Protein of Dane Particles", *Proc. Natl. Acad. Sci. USA*, 78, 3403–3407, 1981; (3) by alterations of antigenicity caused by chemical reagents specifically reacting with distinct amino acid residues, A. R. Neurath and N. Strick, "Localization of a Hepatitis B Surface Antigen Determinant Deduced from Results of Chemical Modifications", *J. Virol. Methods*, 3, 115-125, 1981; or (4) by determining the region of the highest hydrophilicity within the amino sequence of a protein, T. P. Hopp and K. R, Woods, "Prediction of Protein Antigenic Determinants From Amino Acid Sequences", *Proc. Natl. Acad. Sci.*, 78, 3824-3828, 1981.

Immunodominant antigenic determinants may not necessarily be located on a contiguous amino acid sequence representing the primary structure of a protein, but may be composed of residues brought into proximity by the proper folding of the polypeptide chain. Such folding may be stabilized by disulfide bonds between cysteine residues. In such instances, the antigenic determinants may be mimicked by synthetic peptides composed of amino acid residues not directly linked in the sequence of the protein, C. L. Lee and M. Z. Atassi, "Delineation of the Third Antigenic Site of Lysozyme by Application of a Novel 'Surface-Simulation' Synthetic Approach Directly Linking the Conformationally Adjacent Residues Forming the Site", *Biochem. J.*, 159, 89-93, 1976.

Most of the recent studies on synthetic peptides carrying antigenic determinants of viruses or pathogenic microorganisms do not address the issue of whether or not synthetic peptides can protect immunized humans or animals against infection. These studies show, however, that synthetic peptides can either induce antibodies reacting with the "natural" antigen, or conversely that the synthetic peptides can bind at least a portion of antibodies against the "natural" antigen. These studies are not sufficient to show that such synthetic peptides, when used for vaccination, would indeed render humans or animals resistant to infectious agents carrying epitopes (antigen binding sites having a few amino acid residues) homologous with the particular synthetic peptides. In fact, recent reports indicate that antibodies against viral subunits may fail to neutralize the infectivity of the virus, M. M. Hardy and D. M. Moore, "Neutralization of Foot-and Mouth Disease Virus. I. Sensitization of the 140 S Virion by Antibody Also Reactive With the 12 S Protein Subunit", *J. Gen. Virol.*, 55, 415-427, 1981; or that monoclonal antibodies against some viral epitopes may inhibit virus neutralization, R. J. Massey and G. Schochetman, "Viral Epitopes and Monoclonal Antibodies: Isolation of Blocking Antibodies That Inhibit Virus Neutralization", *Science*, 213, 447-450, 1981.

On the other hand, laboratory animals were successfully immunized against diphtheria toxin using a synthetic oligopeptide in F. Audibert et al., "Active Antitoxic Immunization by a Diphtheria Toxin Synthetic Oligopeptide", *Nature*, 289, 593-594, 1981, and a synthetic polypeptide elicited antibodies which promoted phagocytosis and the killing of a pathogenic bacterium in E. H. Beachey et al., "Type-Specific Protective Immunity Evoked By Synthetic Peptide of Streptococcus Pyogenes M Protein", *Nature*, 292, 457-459, 1981.

A synthetic antigen was utilized for the determination of carcinoembryonic antigen levels in sera of cancer patients, R. Arnon et al., "Viroimmunoassay Utilizing a Synthetic Peptide: A Test Equivalent To The Carcinoembryonic Antigen Radioimmunoassay", *Isr. J. Med. Sci.*, 13, 1022-1027, 1977.

A synthetic vaccine comprising a synthetic peptide on a carrier wherein the peptide has a sequence of amino acids corresponding to the sequence of amino acids in a protein, antigen or allergen is described in copending application Ser. No. 223,558, filed Jan. 9, 1981, assigned to the same assignee as the present invention.

Monoclonal antibodies prepared against the natural antigen are described by G. Galfre and C. Milstein, *Methods in Enzymology*, Vol 73, "Immunochemical Techniques, Part B, Preparation of Monoclonal Antibodies: Strategies and Procedures", 1-45, Academic Press, New York, 1981.

Immunoassays utilizing radiolabeled, enzyme labeled, fluorescent or chemiluminescent substances are described in *Methods in Enzymology*, Volumes 70, 73 and 74, "Immunochemical Techniques, Parts A, B, C", Academic Press, New York, 1980-1982; U.S. Pat. No. 4,297,273 to Buckler et al.; A. R. Neurath and N. Strick, "Enzyme-Linked Fluorescence Immunoassays Using β-Galactosidase and Antibodies Covalently Bound to Polystyrene Plates", *J. Virol. Methods*, 1981, 3, 155-165.

The above indicates the need for diagnostic methods relating to the interaction of antibodies (elicited by synthetic peptides) with the corresponding antigens. Such methods would avoid the initial utilization of clinical trials with synthetic vaccines which would be very costly and may potentially involve health risks. The present invention not only satisfies the above described need, but also provides for the utilization of synthetic peptides as diagnostic tools in general for detection of antibodies and antigens.

SUMMARY OF THE INVENTION

In accordance with the present invention there is provided a radiolabeled or enzyme labeled peptide having no more than 60 amino acids in the chain of the peptide. The peptide has covalently linked amino acids disposed in a steric configuration which is recognized by and bound by an antibody.

The present invention also concerns processes for detecting a given antibody in a sample. One such process involves contacting the sample containing the antibody with a solid substrate coated with a non-radiolabeled or non-enzyme labeled peptide having no more than 60 amino acids in the chain of the peptide. The peptide is normally recognized by and bound by an antibody suspected of being present in the sample. The contacted sample is then incubated and washed. The incubated, washed product obtained above is then contacted with a radio labeled or enzyme labeled peptide having less than 60 amino acids in the chain of the peptide. The peptide is normally recognized and bound by the antibody suspected of having been present in the sample. The resultant mass is then incubated and washed and the radioactivity or enzymatic activity is determined.

Another process according to the present invention for detecting the presence of an antibody in a sample involves contacting the sample with a solid substrate coated with a non-radio labeled or non-enzyme labeled peptide having no more than 60 amino acids in the chain of the peptide. The peptide is normally recognized by and bound by the antibody suspected of being present in said sample. The contacted sample is then incubated and washed and then contacted with a radiolabeled or enzyme labeled antibody to human or animal immunoglobulin, such as IgG or IgM. The contacted mass is then incubated and washed and the radioactivity or enzymatic activity is determined.

Another process according to the present invention for the detection of the presence of an antibody in a sample involves contacting the sample with a radiolabeled or enzyme labeled peptide having no more than 60 amino acids in the chain of the peptide. The peptide is normally recognized by and bound by the antibody suspected of being present in said sample. The contacted sample is then incubated and washed. Staphylococci bearing Protein A are then added to the contacted sample with the resultant mass being incubated and centrifuged. The mass is then washed. The radioactivity or enzymatic activity of the resultant pelleted bacteria is then determined.

This invention also provides a process for detecting the presence of antibody or antigen in a sample. The process involves contacting a first portion of a solid substrate coated with antibody which is either an antibody to the antigen suspected in the sample or the same antibody as suspected in the sample, with the sample and with a radiolabeled or enzyme labeled peptide having no more than 60 amino acids in the chain of the peptide. The peptide is normally recognized by and bound by an antibody in the solid substrate. Such contacted first portion is then incubated and washed.

A second portion of the solid substrate coated with the antibody is then contacted with the same amount of the radiolabeled or enzyme labeled peptide in a control. The contacted second portion is then incubated and washed. The radioactivity or enzymatic activity for each contacted portion is then determined.

If the radioactivity or enzymatic activity from the first portion is less than that for the second portion, then the sample is positive for the antibody or antigen in the sample.

The present invention also concerns another process for detecting the presence of an antigen in a sample. The process includes contacting a first portion of a composition containing antibody to the antigen in the sample with a mixture of the sample and a radiolabeled or enzyme labeled peptide having no more than 60 amino acids in the chain of the peptide. The peptide is normally recognized by and bound by the antibody. Then the first portion is incubated and washed.

A second portion of the composition containing antibody is contacted with the same amount of the radiolabeled or enzyme labeled peptide in an antigen free control. The contacted second portion is then incubated and washed.

The same amount of Staphylococci bearing Protein A are then added to each of the first and second contacted portions. Each contacted portion is then incubated and centrifuged and the supernatant liquid is separated from the solids therein and discarded.

The radioactivity or enzymatic activity of the pelleted Staphylococci is then determined. The respective activities from each contacted portion are compared such that if the radioactivity or enzymatic activity for the resultant composition containing the first portion is less than that for the resultant composition containing the second portion, then the sample contains antigen.

The present invention offers the following advantages (1) Easy preparation of large quantities of uniform and well characterized antigens.

(2) Complete elimination of health hazards connected with handling of pathogenic viruses or other microorganisms.

(3) Possibility of preparing reagents with defined antigenic specificity which could be utilized either for broad identification of pathogens sharing common antigenic determinants or for subtyping of related pathogens.

(4) Possibility of wider utilization because of (a) lower costs of reactants as compared with antigens directly corresponding to or derived from pathogens and/or (b) elimination of restrictions in usage to laboratories equipped for work with potentially biohazardous materials.

(5) Possibility of rapidly characterizing antibodies from clinical specimens and of identifying epitopes they are directed against.

BRIEF DESCRIPTION OF DRAWINGS

FIG. 1 is a plot depicting inhibition by HBsAg (hepatitis B surface antigen) of the immunospecific binding to monoclonal anti-HBs (antibodies to HBsAg) coated beads of a $\beta$-galactosidase-conjugated synthetic peptide corresponding to amino acid residues 135–155 of HBsAg.

FIG. 2 is a plot of radioactivity versus dilutions of antiserum containing IgG or IgM antibodies which attached to polystyrene beads coated with HgsAg or P 135–155-KLH (KLH refers to a protein, namely, keyhole lymphet hemocyanin).

DETAILED DESCRIPTION OF THE INVENTION

In one aspect, the present invention concerns a radiolabeled or enzyme labeled peptide. A peptide is two or more amino acids that are linked by the carboxylate group of one amino acid and the ammonium group of another amino acid.

The peptides utilized in the present invention have no more than 60 amino acids in the peptide chain. In a preferred embodiment, the number of amino acids in the peptide chain may range from between about 4 and about 12 amino acids and more preferably between about 4 and about 10 amino acids. The peptide may, on the other hand, for example, have 15 to 30 amino acids in its chain.

Amino acids forming peptides mimicking antigenic determinants can be chosen from the following groups of amino acids: the monoamino, monocarboxylic group including glycine (Gly), alanine (Ala), valine (Val), leucine (Leu) and isoleucine (Ile); the aromatic group including proline (Pro), phenylalanine (Phe), tyrosine (Tyr), tryptophane(Trp) and methionine (Met); the hydroxy group including serine (Ser) and threonine (Thr); the mercapto group including cysteine (Cys); the carboxamide group including asparagine (Asn) and glutamic acid (Gln); the monoamino, dicarboxylic group including aspartic acid (Asp) and glutamic acid (Glu); and the diamino, monocarboxylic group including lysine (Lys), arginine (Arg) and histidine (His). The peptide may also include one or more of the so-called rare amino acids such as, for example, hydroxyproline, cystine and hydroxylysine.

The present invention can be employed as a diagnostic tool to determine the presence of specific antigens, or antibodies to specific antigens by employing peptides which mimic the natural antigens suspected to be present, or the antibodies to such antigens. Thus, for example, the following peptide which mimic the antigenic determinant of natural hepatitis B surface antigen could be used in conjunction with the detection of hepatitis B surface antigens or its corresponding antibodies:

| 135 | 136 | 137 | 138 | 139 | 140 | 141 | 142 | 143        | 144 | 145 |
|-----|-----|-----|-----|-----|-----|-----|-----|------------|-----|-----|
| Pro | Ser | Cys | Cys | Cys | Thr | Lys | Pro | Thr or Ser | Asp | Gly |
| 146 | 147 | 148 | 149 | 150 | 151 | 152 | 153 | 154        | 155 |     |
| Asn | Cys | Thr | Cys | Ile | Pro | Ile | Pro | Ser        | Ser |     |

Alternatively, a smaller amino acid sequence as follows which contains the antigenic determinant for hepatitis B surface antigen can be utilized. T. P. Hopp, "A Synthetic Peptide with Hepatitis B Surface Antigen Reactivity", *Mol. Imm.* 18, 9, 869–872, 1981.

| 138 | 139 | 140 | 141 | 142 | 143 | 144 | 145 | 146 | 147 | 148 | 149 |
|-----|-----|-----|-----|-----|-----|-----|-----|-----|-----|-----|-----|
| Cys | Cys | Thr | Lys | Pro | Thr | Asp | Gly | Asn | Cys | Thr | Cys |

Other peptides mimicking the antigenic determinant of HBsAg include the following:

Peptide (1)

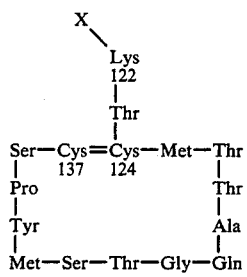

Peptide 2 contains 5 additional amino acid residues:
Ser—Thr—Gly—Pro—Ser—X,
117                    121

G. R. Dreesman, Y. Sanchez, I. Ionescu-Matiu, J. T. Sparrow, H. R. Six, D. L. Peterson, F. B. Hollinger and J. L. Melnick, "Antibody to Hepatitis B Surface Antigen After A Single Inoculation of Uncoupled Synthetic HBsAg Peptides", *Nature*, 295, 158–160, 1982; and (2) the following peptides:

| POSITION | SEQUENCE |
|----------|----------|
| 48–81    | Cys—Leu—Gly—Gln—Asn—Ser—Gln—Ser—Pro—Thr—Ser—Asn—His—Ser—Pro—Thr—Ser—Cys—Pro—Pro—Thr—Cys—Pro—Gly—Tyr—Arg—Trp—Met—Cys—Leu—Arg—Arg—Phe—Ile |
| 2–16     | Glu—Asn—Ile—Thr—Ser—Gly—Phe—Leu—Gly—Pro—Leu—Leu—Val—Leu—Gln—Cys |
| 22–35    | Leu—Thr—Arg—Ile—Leu—Thr—Ile—Pro—Gln—Ser—Leu—Asp—Ser—Trp—Cys |
| 38–52    | Ser—Leu—Asn—Phe—Leu—Gly—Gly—Thr—Thr—Val—Cys—Leu—Gly—Gln—Asn |
| 47–52    | Val—Cys—Leu—Gly—Gln—Asn |
| 95–109   | Leu—Val—Leu—Leu—Asp—Tyr—Gln—Gly—Met—Leu—Pro—Val—Cys—Pro—Leu |
| 104–109  | Leu—Pro—Val—Cys—Pro—Leu |

R. A. Lerner, N. Green, H. Alexander, F.-T. Liu, J. G. Sutcliffe and T. M. Shinnick, "Chemically Synthesized Peptides Predicted From the Nucleotide Sequence of the Hepatitis B Virus Genome Elicit Antibodies Reactive With the Native Envelope Protein of Dane Particles", *Proc. Natl. Acad. Sci. USA*, 78, 6, 3403–3407, 1981.

A peptide containing an amino acid sequence mimicking the antigenic determinant of coliphage MS-2 antigen is as follows:

| 89  | 90  | 91  | 92  | 93  | 94  | 95  | 96  | 97  |
|-----|-----|-----|-----|-----|-----|-----|-----|-----|
| Glu | Leu | Thr | Ile | Pro | Ile | Phe | Ala | Thr |
| 98  | 99  | 100 | 101 | 102 | 103 | 104 | 105 |     |
| Asn | Ser | Asp | Cys | Glu | Leu | Ile | Val |     |

| 106 | 107 | 108  |
|-----|-----|------|
| Lys | Ala | Met, |

R. Arnon, M. Sela, M. Parant and L. Chedid, "Antiviral Response Elicited by A Completely Synthetic Antigen With Built-in Adjuvanticity", *Proc. Natl. Acad. Sci USA*, 77, 11, 6769–6772, 1980.

A peptide containing an amino acid sequence mimicking the antigenic determinant of human leukocyte interferon antigen is as follows:

111
Leu—Met—Asn—Ala—Asp—Ser—Ile—Leu—Ala—Val—Lys—

124  125
Lys—Tyr—Phe—Arg—Arg—Ile—Thr—Leu—Tyr—Leu—Thr—

138  139
Glu—Lys—Lys—Tyr—Ser—Pro—Cys—Ala—Trp—Glu—Val—

152  153
Val—Arg—Ala—Glu—Ile—Met—Arg—Ser—Leu—Ser—Leu—

Ser—Thr—Asn—Leu—Gln—Glu—Arg—Leu—Arg—Arg—

166
                                Lys—Glu

H. Arnheiter, R. M. Thomas, T. Leist, M. Fountlakis, and B. Gutte, "Physicochemical and Antigenic Properties of Synthetic Fragments of Human Leukocyte Interferon", *Nature*, 294, 19, 1981.

A peptide containing an amino acid sequence mimicking the antigenic determinant of human fibroblast interferon is as follows:

| Met | Ser | Tyr | Asn | Leu | Leu | Gly |
|-----|-----|-----|-----|-----|-----|-----|
| Phe | Leu | Gln | Arg | Ser | Ser, |    |

F. Shimizu, Y. Ohmoto and K. Imagawa, "Production of Anti-IFN-β Sera With Chemically Synthetic IFN-β

Peptide Fragment (1-13)", *Biochem and Biophys. Res. Comm.*, 103, 1149-1156, 1981.

A peptide containing an amino acid sequence mimicking the antigenic determinant of retrovirus R antigen is as follows:

Leu Thr Gln Gln Phe His Gln Leu Lys Pro Ile Glu
Cys Glu Pro,

J. G. Sutcliffe, T. M. Shinnick, N. Green, F.-T. Liu, H. L. Niman and R. A. Lerner, "Chemical Synthesis of A Polypeptide Predicted from Nucleotide Sequence Allows Detection of A New Retroviral Gene Product", *Nature,* 287, 1980.

A peptide containing an amino acid sequence mimicking the antigenic determinant of avian sarcoma virus antigen is as follows:

Glu Asp Asn Glu Tyr Thr Ala Arg Gln Gly,

T. W. Wong and Allan R. Goldberg, "Synthetic Peptide Fragment Of src Gene Product Inhibits the src Protein Kinase and Cross reacts Immunologically with Avian onc Kinases and Cellular Phosphoproteins", *Proc. Nat. Acad. USA,* 78, 12, 7412-7416, 1981.

Peptides containing an amino acid sequence mimicking the antigenic determinant of foot-and-mouth disease virus antigen are as follows:

| | | | | | | | | | |
|---|---|---|---|---|---|---|---|---|---|
| 141<br>Val | Pro | Asn | Leu | Arg | Gly | Asp | Leu | Gly | Val |
| Leu | Ala | Gly | Lys | Val | Ala | Arg | Thr | Leu | 160<br>Pro | and

| | | | | | | | | | |
|---|---|---|---|---|---|---|---|---|---|
| 201<br>His | Lys | Gln | Lys | Ile Val | Ala | Pro | Val | Lys | Gln |
| Thr | Leu, | | | | | | | | |

J. L. Bittle, R. A. Houghten, H. Alexander, T. M. Shinnick, J. G. Sutcliffe, R. A. Lerner, D. J. Rowlands and F. Brown, "Protection Against Foot-And-Mouth Disease By Immunization With A Chemically Synthesized Peptide Predicted From the Viral Nucleotide Sequence", *Nature,* 298, 30-33, 1982.

A peptide containing an amino acid sequence mimicking the antigenic determinant of hemagglutinin X-31 (H3N2) influenza virus antigen is as follows:

123 125
Glu—Gly—Phe—Thr—Trp—Thr—Gly—

130 135
Val—Thr—Gln—Asn—Gly—Gly—Ser—

140
Asp—Ala—Cys—Lys—Arg—Gly—Pro—

145 150 151
Gly—Ser—Gly—Phe—Phe—Ser—Arg—Leu,

D. C. Jackson, J. M. Murray, D. O. White, C. N. Fagan and G. W. Tregear, "Antigenic Activity of a Synthetic Peptide Comprising the 'Loop' Region of Influenza Virus Hemagglutinin", *Virology,* 120, 273-276, 1982.

A peptide containing an amino acid sequence mimicking the antigenic determinant of hemagglutinin of type A H3N2 influenza virus antigen was synthesized by G. M. Müller, M. Shapira and R. Arnon, "Anti-influenza Response Achieved by Immunization With A Synthetic Conjugate", *Proc. Natl. Acad. Sci. USA,* 79, 569-573, 1982. The peptide corresponded to the sequence serine-91 to leucine-108 of the amino acid chain of the virus.

A peptide containing an amino acid sequence mimicking the antigenic determinant of polyoma virus medium size tumor antigen is Lys-Arg-Ser-Ars-His-Phe, G. Walter, M. A. Hutchinson, T. Hunter and W. Eckhart, "Purification of Polyoma Virus Medium-Size Tumor Antigen by Immunoaffinity Chromatography", *Proc. Natl. Acad. Sci. USA,* 79, 4025-4029, 1982.

A peptide containing an amino acid sequence mimicking the antigenic determinant of poliovirus replicase antigen is as follows:

Tyr—Ser—Thr—Leu—Tyr—Arg—Arg—Trp—Leu—Asp—
450

Ser—Phe,
461

M. H. Baron and D. Baltimore, "Antibodies Against a Synthetic Peptide of the Poliovirus Replicase Protein: Reaction with Native, Virus-Encoded Proteins and Inhibition of Virus-Specific Polymerase Activities in Vitro", *Jour. Virology,* 43, 3 969-978, 1982.

Peptides containing an amino acid sequence mimicking the antigenic determinant of simian virus 40 large tumor antigen are as follows:

Met-Asp-Lys-Val-Leu-Asn-Arg and

Lys-Pro-Pro-Thr-Pro-Pro-Pro-Glu-Pro-Glu-Thr,

G. Walter, K-H. Scheidtmann, A. Carbone, A. P. Laudano and R. F. Doolittle, "Antibodies Specific for the Carboxy- And Amino-Terminal Regions of Simian Virus 40 Large Tumor Antigen", *Proc. Natl. Acad. Sci USA,* 77, 9, 5179-5200, 1980.

A peptide containing an amino acid sequence mimicking the antigenic determinant of influenza virus strain 3QB antigen is $Ile_1$ $Val_1$ $Asx_2$ $Thr_1$ $Ser_2$ $Glx_2$ $Pro_1$ $Gly_3$ $Ala_1$ $Leu_1$ $Lys_1$, A. Aitken and C. Hannoun, "Purification of Haemagglutinin and Neuraminidase From Influenza Virus Strain 3QB and Isolation of a Peptide From An Antigenic Region Of Haemagluttinin", *Eur. J. Biochem.,* 107, 51-56, 1980.

Peptides containing an amino acid sequence mimicking the antigenic determinant of diptheria antigen are given as follows:

Natural DT Loop

—Cys—Ala—Gly—Asn—Arg—Val—Arg—Arg—Ser—Val—
186 190 195

Gly—Ser—Ser—Leu—Lys—Cys—
201

| Synthetic Peptide | |
|---|---|
| Tetradecapeptide | Gly(188)-Cys—(201) |
| Hexadecapeptide | Cys(186)-Cys—(201) |
| Octadecapeptide | Ala—Ala—Cys(186)-Cys—(201) |

F. Audibert, M. Jolivet, L. Chedid, R. Arnon and M. Sela, "Successful Immunization With A Totally Synthetic Diphtheria Vaccine", *Proc. Natl. Acad. Sci. USA*, 79, 5042-5046, 1982.

A peptide containing an amino acid sequence mimicking the antigenic determinant of Streptococcus pyogenes M antigen is as follows:

```
         5
Asn—Phe—Ser—Thr—Ala—Asp—Ser—Ala—Lys—

10                15
  Ile—Lys—Thr—Leu—Glu—Ala—Glu—Lys—Ala—Ala—

20                25
  Leu—Ala—Ala—Arg—Lys—Ala—Asp—Leu—Glu—Lys—

30                35
                     Ala—Leu—Glu—Gly—Ala—Met
```

E. H. Beachey, J. M. Seyer, D. B. Dale, W. A. Simpson and A. H. Kang, "Type-Specific Protective Immunity Evoked by Synthetic Peptide of Streptococcus Pyogenes M Protein", *Nature*, 292, 457-459, 1981

Indeed, any amino acid sequence which includes at least the antigenic determinant for a specific antigen can be employed in the present invention.

A sequence of amino acids for the human histocompatibility antigen HLA-B7 which determine the antigenic determinant is postulated as Pro Arg Glu Glu Pro Arg corresponding to amino acids 43-48 of the protein.

A sequence of amino acids for the influenza hemaglutinin antigen (X31 strain) which determine the antigenic determinant postulated as Val Glu Arg Ser Lys Ala corresponding to amino acids 105-110 of the protein.

Two sequences of amino acids postulated for the influenza hemagglutinin antigen (Japanese strain) which determine the H-epitopes. These are Glu Lys Glu Asn Pro Arg corresponding to amino acids 96-101 and Lys Glu Asn Pro Arg Asp corresponding to amino acids 97-102.

A sequence of amino acids for the influenza hemagglutinin antigen (Victoria A strain) which determine the antigenic determinant is postulated as Asn Asp Asn Ser Asp Lys corresponding to amino acids 188-193.

Two sequences of amino acids postulated for the Fowl Plague virus hemagglutinin antigen which determine antigenic determinants are as follows: Glu Arg Arg Glu Gly Asn corresponding to amino acids 97-102 and Arg Glu Gly Asn Asp corresponding to amino acid 98-103.

A sequence of amino acids for the human chorionic Gonadotropin B subunit antigen which determine the antigenic determinate is postulated as Arg Arg Ser Thr Thr Asp corresponding to amino acids 94-99.

A sequence of amino acids for the Human Beta-2 microglobulin antigen which determines the antigenic determinant is postulated as Pro Thr Glu Lys Asp Glu corresponding to amino acids 73-78.

A sequence of amino acids for the human Myelin basic protein antigen which determines the antigenic determinant is postulated as Gly Arg Asp Ser Arg Ser corresponding to amino acids 159-164.

A sequence of amino acids for the Cholera Toxin B-chain antigen which determines the antigenic determinant is postulated Glu Ala Lys Val Glu Lys corresponding to amino acids 79-84.

A sequence of amino acids for the E Coli Heat Labile Toxin which determine the antigenic determinant is postulated as Glu Arg Met Lys Asp Thr corresponding to amino acids 66-71

A sequence of amino acids for the E. Coli Heat Stabile Toxin provides two identical antigenic determinants whose amino acid sequence is postulated as Asp Ser Ser Lys Glu Lys and Ser Glu Lys Lys Ser Glu correspond to amino acids 26-31 and 46"41, respectively.

The streptococcal M protein (strain 24) has two identical antigenic determinants whose amino acid sequences are postulated as Arg Lys Ala Asp Leu Glu and Lys Ala Asp Leu Glu Lys corresponding to amino acids 58-63 and 59-64, respectively.

The trypanosoma brucei variant surface glycoprotein 117 has an antigenic determinant whose amino acid sequence is postulated as Lys Ala Lys Glu Lys Gly corresponding to amino acids 50-55.

In synthetic peptides according to the invention, it is preferred to attach the amino acids which define the antigenic determinants (usually five or six amino acids) to at least three amino acids on either side thereof. These three amino acids can be the same acids in the same sequence as they occur in the natural protein. However, other amino acids can also be used. It is also possible to employ a peptide having more than one antigenic determinant.

The peptide of this invention can be formed "naturally" or "synthetically". In the natural formation of the peptide, a protein containing the required amino acid sequence is subjected to selective proteolysis such as by splitting the protein with chemical reagents or using enzymes. Synthetic formation of the peptide requires chemically synthesizing the required chain of amino acids.

Isolation of peptides from natural sources: If sufficient quantities of the whole protein antigen are available, a limited portion of the molecule, bearing the required sequence of amino acids, may be excised by any of the following procedures:

(a) Digestion of the protein by proteolytic enzymes, specially those enzymes whose substrate specifically results in cleavage of the protein at sites immediately adjacent to the desired sequence of amino acids.

(b) Cleavage of the protein by chemical means. Particular bonds between amino acids can be cleaved by reaction with specific reagents. Examples include: bonds involving methionine are cleaved by cyanogen bromide; asparaginyl glycine bonds are cleaved by hydroxylamine; disulfide bonds between two cysteine residues are cleaved by reduction, e.g., with dithiothreitol.

(c) A combination of proteolytic and chemical changes. It should also be possible to clone a small portion of the DNA that codes for the synthetic peptide, resulting in the production of the peptide by bacteria.

The biologically derived peptide, once produced, may be purified by gel filtration, ion exchange or high pressure liquid chromatography, or other suitable means.

Chemical synthesis of peptides is described in the following publications: S. B. H. Kent, *Biomedical Polymers*, eds. Goldberg, E. P. and Nakajima, A. (Academic Press, New York), 213–242, 1980; A. R. Mitchell, S. B. A. Kent, M. Engelhard, and R. B. Merrifield, *J. Org. Chem.* 43, 2845–2852, 1978; J. P. Tam, T.-W. Wong, M. Riemen, F.-S. Tjoeng, and R. B. Merrifield, *Tet. Letters*, 4033–4036, 1979; S. Mojsov, A. R. Mitchell, and R. B. Merrifield, *J. Org. Chem.* 45, 555–560, 1980; J. P. Tam, R. D. Di Marchi and R. B. Merrifield, *Tet. Letters*, 2851–2854, 1981; and S. B. H. Kent, M. Riemen, M. Le Doux and R. B. Merrifield, *Proceedings of the IV International Symposium on Methods of Protein Sequence Analysis*, (Brookhaven Press, Brookhaven, N.Y.), in press, 1981.

The "Merrifield solid phase procedure" as described in the above-mentioned publications can be used to build up the appropriate sequence of L-amino acids from the carboxyl terminal amino acid to the amino terminal amino acid. Starting with the appropriate carboxyl terminal amino acid attached to a polystyrene (or other appropriate) resin via chemical linkage to a chloromethyl group, benzhydrylamine group, or other reactive group of the resin, amino acids are added one by one using the following procedure for each:

(a) Peptidyl resin is washed with methylene chloride;

(b) the resin is neutralized by mixing for 10 minutes at room temperature with 5% (v/v) diisopropylethylamine (or other hindered base) in methylene chloride;

(c) the resin is washed with methylene chloride;

(d) an amount of amino acid equal to six times the molar amount of the growing peptide chain is activated by combining it with one-half as many moles of a carbodiimide, e.g., dicyclohexylcarbodiimide, diisopropylcarbodiimide, for 10 minutes at 0° C., to form the symmetric anhydride of the amino acid. The amino acid used should be provided originally as the N-α-butyloxycarbonyl derivative, with side chains protected with benzyl esters (aspartic and glutarmic acids), benzyl ethers (serine, threonine, cysteine, tyrosine), benzyl oxycarbonyl groups (lysine) or other protecting groups commonly used in peptide synthesis;

(e) the activated amino acid is reacted with the peptidyl resin for 2 hours at room temperature resulting in addition of the new amino acid to the end of the growing peptide chain;

(f) the resin is washed with methylene chloride;

(g) the N-α-(butyloxycarbonyl) group is removed from the most recently added amino acid by reacting with 30% (v/v) trifluoracetic acid in methylene chloride for 30 minutes at room temperature;

(h) the resin is washed with methylene chloride;

(i) steps a through h are repeated until the required peptide sequence has been constructed. The peptide is then removed from the resin and simultaneously the side-chain protecting groups are removed, by reacting with anhydrous hydrofluoric acid containing 10% (v/v) of anisole. Subsequently, the peptide can be purified by gel filtration, ion exchange, or high pressure liquid chromatography, or other suitable means.

Chemical synthesis can be carried out without a solid phase resin, in which case the synthetic reactions are performed entirely in solution. The reactions, and the final product, are otherwise essentially identical.

The peptide of this invention is labeled either by a radioactive tracer or by an enzyme. Such labeling means are well known in the art. Some peptides are, however, difficult to radiolabel. If, for example, the peptide does not contain tyrosine, it may be necessary to use an intermediate compound prior to radiolabeling. One such compound is a non-tyrosine containing peptide having no more than 60 amino acids, to which is bonded via a lysine moiety or a terminal amino acid a 3(p-hydroxyphenyl)propionyl. This intermediate compound may be formed by combining the peptide with a Bolton-Hunter reagent such as

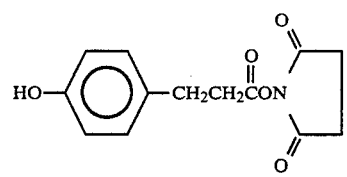

at a temperature of between about 0° C. and about 50° C. for between about 0.25 hours and 4 hours, at an alkaline pH of between about 8 and about 9, using 1 to 2 times the stoichiometric amounts of the reagent per labeling site. The intermediate that forms is as follows:

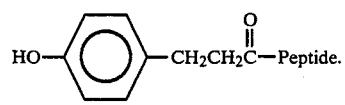

This intermediate is then contacted with a radioactive material such as, for example, radioactive iodine as described hereinbelow.

If the peptides does contain tyrosine, it can be labeled by contacting the peptide with $NaI^{125}$ in a buffer and then oxidizing it in the presence of an oxidizing agent such as chloramine T.

In the process of this invention the peptide can exist in free form or can be attached to a soluble carrier, such as a protein or a synthetic polymer. Non-limiting examples of protein carriers include keyhole lymphet hemocyanin, Limulus polyphemus hemocyanin and bovine serum albumin. When a carrier is used, the carrier itself can be labeled and attached to an unlabled peptide so as to form a labeled peptide-carrier conjugate (which can serve as a "labeled peptide").

The peptide utilized in this invention can be employed with or without a solid support (substrate). A non-limiting example of a solid support that may be employed is polystyrene beads.

In one process according to the present invention for detection of a given antibody in a sample, the sample is contacted with a solid substrate containing a non-radiolabeled or non-enzyme labeled peptide. The substrate can be substantially free of available protein binding site. The substrate can have a protein binding site occupier, such as, for example, albumin, bound thereto to prevent or reduce non-specific binding.

The peptide utilized in the processes of this invention has no more than 60 amino acids in the chain of the peptide. The peptide is normally recognized by and bound by the antibody suspected of being present in the sample.

The contacted sample is incubated, washed and then contacted with a radiolabled or enzyme labeled synthetic peptide, such peptide as defined above. The resultant mass is incubated and washed.

The incubation steps required in carrying out the invention can be effected in known manner, such as by incubating antigen with labeled antibody at temperatures of between about 37° C. and about 50° C. for between about 1 hour and about 8 hours or between about 18° C. and about 30° C. for between about 16 hours and about 72 hours.

Washings are typically effected using an aqueous solution such as one buffered at a pH of 6–8, preferably at a pH of about 7, employing an isotonic saline solution.

Without wishing to be bound by any particular theory of operability, it is believed that the antibody in the above process binds to one end of the support, allowing the labeled peptide to bind the other end of the antibody. If there is no antibody binding with the support, there would be no binding of the labeled peptide, except for non-specific binding. Accordingly, the more antibody binding, the greater the binding of the labeled peptide and the higher the radioactivity or enzymatic activity.

In another process to detect antibodies in a sample according to the present invention, the sample is contacted with a solid substrate containing a peptide (peptide is not labeled). The solid substrate is washed and exposed to labeled antibody to human or animal immunoglobulin. The presence of radioactivity or enzymatic activity would indicate the sample was antibody positive.

In a further process to detect antibodies in a sample according to the present invention, a labeled peptide is contacted with a sample suspected of containing antibodies and with Staphylococci bearing Protein A. The Staphylococci bearing Protein A attaches immune complexes of antigens and antibodies or antibodies in free form. Accordingly, an antibody in the sample will bind with the bacteria and the labeled peptide which reacted with the antibodies will also become bound. In the absence of antibodies, the labeled peptide will not bind to the Staphylococci.

The present invention also concerns competition tests to detect antigens in a sample. A labeled synthetic peptide can be used to detect antigens by competition between the labeled synthetic peptide and the antigen in the sample.

In one process according to the present invention for detecting the presence of antigens or antibodies, the sample suspected of containing antigens or antibodies is contacted with antibody (to the suspected antigen or the same antibody as suspected in the sample) coated polystyrene beads and a labeled peptide, said peptide as defined hereinabove. Similar antibody coated beads contacted with a labeled peptide (no sample present) are maintained as a control. If the radioactivity or enzymatic activity is lower for the beads which contact the sample as compared to the control, then antigen or antibody is present in the sample.

If antibodies were present in the sample, then they would compete with the antibodies on the beads and hence fewer labeled peptides would bind to the beads and thus lowering the radioactivity or enzymatic activity of the polystyrene beads.

If antigens were present in the sample they would compete with the antibodies on the beads for binding with the labeled peptide, hence less labeled peptide would bind on the beads resulting in a lower radioactivity or enzymatic acitivity.

In another process to detect antigens according to the present invention, a sample is contacted with an antibody to the suspected antigen and a labeled peptide. A second portion of the antibody composition with a labeled peptide is maintained as an antigen free control. Staphylococci bearing Protein A are added to both portions. Radioactivities or enzymatic activities are determined for both portions. The antigen in in the sample, if any, will compete with the labeled peptide for the antibody. If the radioactivity or enzymatic activity for the control portion is higher, then the sample contains antigen.

The invention will now be described in further detail by reference to the following specific, non-limiting examples.

EXAMPLE 1

A synthetic peptide carrying a major antigenic determinant of HBsAg (hepatitis B surface antigen) was prepared. The selection of an amino acid sequence carrying a major antigenic determinant of HBsAg is described in A. R. Neurath, N. Strick, N. R. Oleszko, "Localization of a Hepatitis B Surface Antigen Determinant Deduced From Results of Chemical Modifications", *J. Virol. Methods,* 3, 115–125, 1981. The amino acid sequence is as follows:

| 135 | 136 | 137 | 138 | 139 | 140 | 141 | 141 | 143 | 144 | 145 |
|---|---|---|---|---|---|---|---|---|---|---|
| Pro | Ser | Cys | Cys | Cys | Thr | Lys | Pro | Thr or Ser | Asp | Gly |
| 146 | 147 | 148 | 149 | 150 | 151 | 152 | 153 | 154 | 155 | |
| Asn | Cys | Thr | Cys | Ile | Pro | Ile | Pro | Ser | Ser | |

(The above numbers indicate the position of each amino acid in the sequence of the "natural" HBsAg polypeptide).

The above described peptide was prepared according to the procedure described in S. B. H. Kent, H. Riemen, M. Le Doux, and R. B. Merrifield, *Proceedings of the IV International Symposium on Methods of Protein Sequence Analysis,* (Brookhaven Press, Brookhaven, N.Y.), 1981, in press.

EXAMPLE 2

Enzyme labeling of the synthetic peptide carrying a major antigenic determinant of HBsAg One mg of the synthetic peptide with the amino acid sequence listed above in Example 1 was dissolved in 0.1M NaCl, 0.1M phosphate pH 7.5 (PBS) and treated with mercaptoethanol (10 mg/ml) for one hour at 20° C. The reduced peptide was subjected to gel filtration on a column (0.7×20 cm) of Sephadex G-10 (Pharmacia Fine Chemicals AB, Uppsala, Sweden and Piscataway, N.J.) using PBS as an eluent. Fractions corresponding to the peak of optical density (OD) at 220 nm were pooled and 0.5 mg of solid E. coli β-galactosidase were added. After standing, overnight at room temperature, the enzyme-peptide conjugate was subjected to gel-filtration on Sephadex G-50 using PBS as an eluent. Fractions corresponding to the void volume of the column were pooled and used for immunoassays.

EXAMPLE 3

Preparation of antibodies to the synthetic peptide carrying a major antigenic determinant of HBsAg For immunization of rabbits and development of immunoassays, synthetic peptides as defined above were covalently linked to keyhole limpet hemocyanin (KLH; Calbiochem-Behring), Limulus polyphemus hemocyanin (LPH; Sigma Chemical Co., St. Louis, Mo.), bovine serum albumin (BSA) and β-galactosidase (~600 U/mg; Boehringer Mannheim Biochemicals, Indianapolis, Ind., respectively. One mg quantities of each of the above peptides in 500 µl of 0.1M NaCl, 0.1M sodium phosphate, pH 7.5 (PBS) were mixed with 2-mercaptoethanol (final concentration 10 mg/ml) for 1 hour at room temperature. The reduced peptides were separated from 2-mercaptoethanol by chromatography on a 0.7×20 cm column of Sephadex G-10 (Pharmacia Fine Chemicals AB, Upsala, Sweden and Piscataway, N.J.). The void volume fraction containing the peptide were pooled and mixed either with 500 µg of β-galactosidase or with 5 mg or either keyhole limphet hemocyanin, Limulus polyphemus hemocyanin, or bovine serum albumin, with an additional SH group introduced using the heterobifunctional reagent N-succinimidyl-3-(2-pyridyldithio)-propionate (SPDP). After standing overnight at room temperature, the protein-peptide conjugates were separated from unbound peptide by chromatography on Sephadex G-50. The coupling efficiency, determined from measurements of A at 280 and 220 nm, was between 20 and 30%.

Conjugates containing approximately 200 peptide molecules per KLH or LPH molecule were mixed 1:1 with complete Freund's adjuvant and injected into rabbits (approximately 70 µg of peptide/rabbit). The rabbits were further injected in biweekly intervals with equal doses of conjugates in incomplete Freund's adjuvant. Blood specimens were taken 2 weeks after each injection. Mice were immunized similarly with 10 times less antigen.

The rabbits were bled two weeks after each injection and serum specimens were tested by a commercial radioimmunoassay (RIA) for antibodies to HBsAg (Ausab test, Abbott Laboratories, North Chicago, Ill.). All serum specimens taken from the rabbit were strongly positive in the test indicating that the synthetic peptide induced antibodies to HBsAg. The carrier protein keyhole lymphet hemocyanin alone failed to induce antibodies to HBsAg. A control conjugate consisting of keyhole lymphet hemocyanin and a synthetic human insulin A chain also failed to elicit antibodies to HBsAg.

EXAMPLE 4

Immunoassays using antibodies to a synthetic polypeptide and enzyme-conjugated peptide It is known that immunoglobulins of the IgG class attach to Staphylococci carrying protein A. If the immunoglobulins are bound to labeled antigens thus forming immune complexes, such (labeled) complexes attach to the Staphylococci. In the presence of unlabeled antigens, the binding of labeled antigens to IgG, and consequently also to Staphylococci, is competitively suppressed. The above forms the basis of the following test:

250 µl of mixtures containing various unlabeled antigens, 1:125 diluted antiserum to the synthetic peptide (see Example 3 above), 1:8,000 diluted peptide-β-galactosidase conjugate (see Example 2 above) and 50 mg/ml of bovine serum albumin (BSA) were each incubated for 30 minutes at 37° C. and mixed with an equal volume of a 2.5% suspension of Staphylococci (Pansorbin, Calbiochem, LaJolla, Calif.). The bacteria were pelleted, washed with tris-buffered saline, and the adsorbed β-galactosidase corresponding to the enzyme-peptide conjugate was determined fluorometrically as described by Neurrath and Strick, *J. Virol. Methods,* supra. The fluorescence in the absence of unlabeled competing antigens was 900. When normal rabbit serum was used instead of the antiserum to the synthetic peptide the fluorescence was 22, indicating that the β-galactosidase-peptide conjugate was immunospecifically bound to IgG antibodies from the immunized rabbit.

Intact HBsAg and distinct synthetic peptides caused inhibition of binding of β-galactosidase activity to the bacteria (see Table 1, hereinafter). This inhibition represents the basis for quantitation of the various unlabeled antigens related to the antigen-β-galactosidase conjugate. Control antigens (synthetic insulin A chain and keyhole lymphet hemocyanin) did not have any inhibitory effect in the test. Much higher amounts of intact HBsAg, than of synthetic peptides, were required to observe measurable inhibition. This is due to the following: (1) the fact that the sequence within HBsAg corresponding to the synthetic peptide (residues 135-155) represents only about 9% of the total mass of the major "natural" HBsAg polypeptide and (2) antibodies induced by the synthetic peptide preferably bind to the immunizing antigen rather than to HBsAg. This latter finding, which was confirmed by additional experiments involving affinity chromatography, suggests the need for better designed synthetic peptides with defined three-dimensional structures more closely resembling the relevant region of HBsAg.

EXAMPLE 5

Immunoassays using monoclonal antibodies to HBsAg and enzyme-conjugated synthetic peptide Polystyrene beads coated with six distinct monoclonal antibodies to intact HBsAg and isolated from distinct clones of mouse hybridoma cells were incubated with a 1:5,000-fold diluted peptide-β-galactosidase conjugate (see Example 2 above) in tris-buffered saline containing 50 mg/ml of bovine serum albumin for 2 hours at 37° C. The beads were washed, and the adsorbed β-galactosidase activity was determined as described in the preceding examples. Strong binding of the enzyme conjugate (P 135-155-β-galactosidase) was observed with only one out of the six sets of beads coated with distinct monoclonal antibodies (IgM antibody having a K for HBsAg binding of $4 \times 10^{11} \times M^{-1}$). The corresponding beads were selected for further studies. The binding of the peptide-enzyme conjugate was suppressed by approximately 50% in the presence of either intact HBsAg (5 µg) or of the peptides (20 µg of each) listed in Table 1, hereinbelow.

In subsequent tests, the beads were preincubated with 0.4 ml of 5% bovine serum albumin in tris-buffered saline containing various amounts of HBsAg, for 30 minutes at 37° C. Subsequently, the peptide-β-galactosidase conjugate was added to a final concentration of 1:8,000 and the beads were incubated for 2 hours at 37° C. The adsorbed enzyme was detected as described above.

Results presented in FIG. 1 indicate that nanogram (ng) quantities of HBsAg can be detected on the basis of its inhibitory effect on binding of the peptide-β-galactosidase conjugate to the beads.

FIG. 1 illustrates inhibition by HBsAg of P-135-155-β-galactosidase binding to polystyrene beads coated with monoclonal IgM anti-HBs. Quantities of HBsAg indicated in the abscissa of the plot of FIG. 1 and dissolved in 400 μl of tris-buffered saline containing 50 mg/ml bovine serum albumin were added to the beads and incubated for 30 minutes at 37° C. P135-155-β-galactosidase (~4 ng) in 100 μl of tris-buffered saline was added to the beads followed by incubation for 2 hours at 37° C. The beads were washed with tris-buffered saline and β-galactosidase attached to the beads was determined as described above. The percent inhibition of P135-155-β galactosidase binding was calculated by comparison with controls to which HBsAg was not added.

TABLE 1

Inhibition by HBsAg and by synthetic peptides corresponding to amino acid residues of HBsAg (indicated by the first and last residue numbers) of the binding to Staphylococci of β-galactosidase-conjugated peptide 135-155 complexed with homologous antibodies.

| Absolute quantity of inhibitor | % Inhibition with Peptides | | | | | |
|---|---|---|---|---|---|---|
| | 150-155 | 149-155 | 145-155 | 140-155 | 135-155 | HBsAg |
| 100 μg | | | | | | 21.5 |
| 10 μg | | | | | | 14 |
| 2 μg | 61 | 94 | 89 | 88 | 88.2 | 0 |
| 200 ng | 54 | 86.3 | 75.2 | 53 | 65.5 | 0 |
| 20 ng | 27 | 45 | 30 | 48.5 | 37 | 0 |
| 2 ng | 4.5 | 25 | 16 | 28.5 | 29 | 0 |

EXAMPLE 6

IgG and IgM antibodies to HBsAg elicited by the synthetic peptide P135-155 were determined by RIA (radioimmunoassay) using radiolabeled anti-IgG and anti-IgM Dilutions of rabbit sera (expected to contain anti-HBs) in a mixture of normal fetal calf serum and normal goat serum 9:1, adjusted to pH 8.5 and containing 1 mg/ml of Tween 20, were added to polystyrene beads coated with HBsAg (supplied as part of the Ausab kit from Abbott Laboratories). After incubation overnight at room temperature, the beads were washed with tris-buffered saline and incubated with [$^{125}$I] anti-rabbit IgG (or IgM) (approximately $10^5$ cpm in fetal calf serum-goat serum 9:1) for 2 hours at 37° C. The beads were then washed with tris-buffered saline and counted in a γ-counter. To correct for nonspecific adsorption of immunoglobulins to the beads, dilutions of normal rabbit sera were tested in the same way. The results were subtracted from the counts per minute (cpm) corresponding to the same dilutions of sera expected to contain anti-HBs.

Similar tests to the above were carried out with human sera. Goat anti-human IgM, and anti-rabbit IgG and IgM were obtained from Kirkegaard & Perry Laboratories, Inc., Gaithersburg, Md.; Calbiochem-Behring, La Jolla, Calif. and Cappel Laboratories, Cochranville, Pa., respectively. The antibodies were immunochemically purified, except the anti-rabbit IgM which was isolated from serum by chromatography on DEAE-cellulose, and labeled with [$^{125}$I] using Iodo-Beads (Pierce Chemical Company, Rockford, Ill.) in accordance with the manufacturer's instructions.

EXAMPLE 7

Radioactive Labeling of Peptide

To label peptide 135-155 (P135-155) with [$^{125}$I], it was necessary to introduce phenyl residues. This was accomplished by reacting 500 μg of the peptide with a 10-fold molar excess of 3(p-hydroxyphenyl)propionic acid N-hydroxysuccinimidiyl ester (Tagit reagent, Calbiochem) in 0.05M borate, pH 8.5 for 2 hours at 0° C. Excess reagent was separated by chromatography on Sephadex G-15 using PBS as an eluent. An aliquot (approximately 20 μg) of the derivatized peptide, recovered in the void volume of the column, was labeled with 200 μCi of Na[$^{125}$I] using Iodobeads. The labeled product was separated from excess [$^{125}$I] by chromatography on Sephadex G-15 and diluted in tris buffered saline containing 10 mg/ml BSA to 100,000 cpm/100 μl (=37.5 pmoles peptide/100 μl).

Antibodies to P135-155 were assayed by the following methods:

(1) Serial dilutions of sera in tris-buffered saline (250 μl) were each mixed with the P135-155-β-galactosidase conjugate (approximately 5 ng of each enzyme and peptide), incubated 30 minutes at 37° C. and mixed with 100 μl of a 10% suspension of Staphlococci bearing protein A (Pansorbin, Calbiochem). After standing for 30 minutes at room temperature, the bacteria were pelleted by centrifugation and washed two times with tris-buffered saline. β-galactosidase activity in the immune complex attached to the bacteria was determined fluorometrically. This method measured IgG antibodies.

(2) [$^{125}$I]-labeled P135-155 was used instead of the P135-155-β-galactosidase conjugate in tests similar to (1) above.

(3) Polystyrene beads were coated with either P135-155-KLH or P135-155-BSA to measure anti-P135-155 elicited by keyhole limpet homocyanin or Limulus polyphemus hemocyanin conjugates, respectively, under conditions described above IgG or IgM antibodies to P135-155 were assayed using [$^{125}$I]-labeled antibodies to rabbit (or human) IgG or IgM as described above for tests of anti-HBs.

Antibodies to the protein carrier (KLH) were assayed similarly except that beads coated with KLN only were used.

FIG. 2 depicts the relationship between IgG (●, o) or IgM (▲,Δ) antibodies attached to polystyrene beads precoated with HBsAg (●, ▲) and P135-155-KLH (o, Δ), respectively, and dilutions of a serum from a rabbit immunized twice with P135-155-LPH. The attached antibodies were detected with [$^{125}$I]-labeled anti-rabbit IgG and IgM, respectively. The attachment of IgG antibodies (from a rabbit immunized with HBsAg) to beads precoated with HBsAg (■) is shown for comparison. LPH and KLH do not cross-react immunologically.

The present invention may be embodied in other specific forms without departing from the spirit or essential attributes thereof and, accordingly, reference should be made to the appended claims, rather than to the foregoing specification, as indicating the scope of the invention.

What is claimed is:

1. A process for the detection of antibodies to Hepatitis B in a sample which comprises:
   a. contacting said sample with a solid substrate coated with an unlabeled synthetic peptide comprising the following sequence of amino acids: Pro Ser Cys Cys Cys Thr Lys Pro Thr or Ser Asp Gly Asn Cys Thr Cys Ile Pro Ile Pro Ser Ser, which peptide is recognized by and bound by the antibodies suspected of being present in said sample, incubating and washing said contacted sample,
   b. contacting the incubated, washed mass obtained from step a. above with a radiolabeled or enzyme labeled antibody to human or animal immunoglobulin, incubating and washing the contacted sample, and
   c. determining the radioactivity or enzymatic activity of the resultant mass of step b. above.

2. A process for the detection of the presence of an antibody to Hepatitis B in a sample which comprises:
   a. contacting said sample with a radiolabeled or enzyme labeled synthetic peptide comprising the following sequence of amino acids: Pro Ser Cys Cys Cys Thr Lys Pro Thr or Ser Asp Gly Asn Cys Thr Cys Ile Pro Ile Pro Ser Ser, which peptide is recognized by and bound by the antibody suspected of being present in said sample, incubating and washing said contacted sample,
   b. adding Staphylococci bearing Protein A to said contacted sample, incubating and centrifuging the resultant mass,
   c. washing the resultant mass and
   d. determining the radioactivity or enzymatic activity of the resultant pelleted bacteria.

3. A process for detection of the presence of an antibody to Hepatitis B or Hepatitis B surface antigen in a sample which comprises
   a. contacting a first portion of a solid substrate coated with antibody with a mixture of said sample and a radiolabeled or enzyme labeled synthetic peptide having no more than 60 amino acids in the chain of the peptide, which amino acids mimic at least one antigenic determinant of a natural antigen, which peptide is recognized by and bound by the antibody in said solid substrate, incubating and washing said contacted first portion, to obtain a first resultant composition, wherein the peptide comprises the following sequence of amino acids:

Pro Ser Cys Cys Thr Lys Pro Thr or

Ser Asp Gly Asn Cys Thr Cys Ile Pro Ile Pro Ser Ser;

b. in a control, contacting a second portion of said solid substrate coated with said antibody with the same amount of said radiolabeled or enzyme labeled peptide as in step a. above, incubating and washing said contacted second portion, to obtain a second resultant composition,
   c. detecting the radioactivity or enzymatic activity of said first resultant composition from step a. above, and
   d. determining the radioactivity or enzymatic activity of said second resultant composition from step b. above, and
   e. comparing activities from steps c. and d. above, such that if the radioactivity or enzymatic activity from step c. is less than from step d., then the sample is positive for the antibody in the sample.

4. A process for detecting the presence of Hepatitis B surface antigen in a sample which comprises:
   a. contacting a first portion of a composition containing an antibody to said antigen with a mixture of said sample and a radiolabeled or enzyme labeled synthetic peptide having no more than 60 amino acids in the chain of the peptide, which amino acids mimic at least one antigenic determinant of a natural antigen, which peptide is recognized by and bound by said antibody, incubating and washing said first portion, wherein the peptide comprises the following sequence of amino acids:

Pro Ser Cys Cys Cys Thr Lys Pro Thr or

Ser Asp Gly Asn Cys Thr Cys Ile Pro Ile Pro Ser Ser, b. contacting a second portion of said composition containing antibody with the same amount of said radiolabeled or enzyme labeled peptide in an antigen free control, incubating and washing said second portion,
   c. adding the same amount of Staphylococci bearing protein A to each of the compositions of steps a. and b. above, incubating both of said compositions, centrifuging each of said compositions and separating the supernatant liquid from the solids therein,
   d. determining the radioactivity or enzymatic activities of each of the resultant compositions from step c, above, and
   e. comparing the respective radioactivity or enzymatic activity from step d. above such that if the activity for the resultant composition containing the first portion is less than the activity for the resultant composition containing the second portion, then the sample contains antigen.

5. A process for the detection of antibodies to Hepatitis B surface antigen in a sample which comprises:
   a. contacting said sample with a solid substrate coated with an unlabeled synthetic peptide having no more than 60 amino acids in the chain of the peptide which amino acids mimic at least one antigenic determinant of a natural antigen, which peptide is recognized by and bound by the antibody suspected of being present in the sample, incubating and washing said contacted sample, wherein the peptide comprises the following sequence of amino acids:

Cys Cys Thr Lys Pro Thr Asp Gly Asn Cys Thr Cys, b. contacting the incubated, washed mass obtained from step a. above with:

a radiolabeled or enzyme labeled peptide having less than 60 amino acids in the chain of the peptide, which amino acids mimic said antigenic determinant or determinants, which peptide is recognized by and bound by the antibody suspected of having been present in said sample, said peptide comprising the following sequence of amino acids:

Cys Cys thr Lys Pro Thr Asp Gly Asn Cys Thr Cys, or with a radiolabeled or enzyme labeled antibody to human or animal immunoglobulin, incubating and washing the resultant mass, and c. determining the radioactivity or enzymatic activity of the resultant mass of step b. above.

6. A process for the detection of antibodies to Hepatitis B surface antigen in a sample which comprises:

a. contacting said sample with a radiolabeled or enzyme labeled synthetic peptide having no more than 60 amino acids in the chain of the peptide, which amino acids mimic at least one antigenic determinant of a natural antigen, which peptide is recognized by and bound by the antibody suspected of being present in said sample, incubating and washing said contacted sample, wherein the peptide comprises the following sequence of amino acids:

Cys Cys Thr Lys Pro Thr Asp Gly Asn Cys Thr Cys, b. adding Staphylococci bearing Protein A to said contacted sample, incubating and centrifuging the resultant mass, c. washing the resultant mass and d. determining the radioactivity or enzymatic activity of the resultant pelleted Staphylococci bacteria.

7. A process for detecting the presence of a Hepatitis B surface antigen in a sample which comprises:

a. contacting a first portion of a solid substrate coated with antibody which is an antibody to the antigen suspected in same sample with a mixture of said sample and a radiolabeled or enzyme labeled synthetic peptide selected from the group consisting of Pro Ser Cys Cys Cys Thr Lys Pro Thr,
Ser Asp Gly Asn Cys Thr Cys Ile Pro Ile Pro Ser Ser,
Cys Cys Thr Lys Pro Thr Asp Gly Asn Cys Thr Cys, -continued

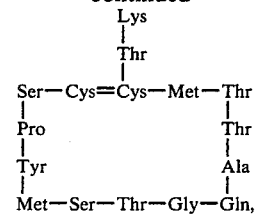

Ser—Thr—Gly—Pro—Ser —Lys

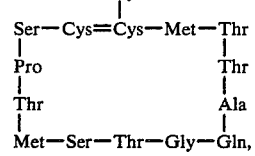

Cys—Leu—Gly—Gln—Asn—Ser—Gln—Ser—Pro—Thr—
Ser—Asn—His—Ser—Pro—Thr—Ser—Cys—Pro—Pro—
Thr—Cys—Pro—Gly—Thr—Arg—Trp—Met—Cys—Leu—
Arg—Arg—Phe—Ile,

Glu—Asn—Ile—Thr—Ser—Gly—Phe—Leu—
Gly—Pro—Leu—Leu—Val—Leu—Gln—Cys,

Leu—Thr—Arg—Ile—Leu—Thr—Ile—Pro—
Gln—Ser—Leu—Asp—Ser—Trp—Cys,

Ser—Leu—Asn—Phe—Leu—Gly—Gly—Thr—
Thr—Val—Cys—Leu—Gly—Gln—Asn,

Val—Cys—Leu—Gly—Gln—Asn,

Leu—Val—Leu—Leu—Asp—Tyr—Gln—Gly—
Met—Leu—Pro—Val—Cys—Pro—Leu and

Leu—Pro—Val—Cys—Pro—Leu, which peptide is recognized by and bound by the antibody in said solid substrate, incubating and washing said contacted first portion, to obtain a first resultant composition, b. in a control, contacting a second portion of said solid substrate coated with said antibody with the same amount of said radiolabeled or enzyme labeled peptide as in step a. above, incubating and washing said contacted second portion, to obtain a second resultant composition, c. detecting the radioactivity or enzymatic activity of said first resultant composition from step a. above, d. determining the radioactivity or enzymatic activity of said second resultant composition from step b. above, and e. comparing activities from steps c. and d. above, such that if the radioactivity or enzymatic activity from step c. is less than from step d., then the sample is positive for the antigen in the sample.

8. A process for the detection of Hepatitis B surface antigen in a sample according to claim 7 wherein said synthetic peptide is enzyme labeled.

* * * * *